United States Patent
Marzano et al.

(10) Patent No.: US 9,114,149 B2
(45) Date of Patent: Aug. 25, 2015

(54) [CU(THP)4]N[X]-N COMPOUNDS FOR THE TREATMENT OF A BROAD RANGE OF HUMAN SOLID TUMORS, INCLUDING REFRACTORY TUMORS

(75) Inventors: Cristina Marzano, Padua (IT); Marina Porchia, Padua (IT); Francesco Tisato, Padua (IT); Valentina Gandin, Padua (IT); Carlo Santini, Camerino (IT); Maura Pellei, Camerino (IT); Giancarlo Gioia Lobbia, Camerino (IT); Grazia Papini, Camerino (IT)

(73) Assignees: Universita Degli Studi Di Padova, Padua (IT); Universita Degli Studi Di Camerino, Camerino (Macerata) (IT)

( * ) Notice: Subject to any disclaimer, the term of this patent is extended or adjusted under 35 U.S.C. 154(b) by 0 days.

(21) Appl. No.: 14/238,466

(22) PCT Filed: Aug. 16, 2011

(86) PCT No.: PCT/IB2011/053624
§ 371 (c)(1),
(2), (4) Date: Feb. 11, 2014

(87) PCT Pub. No.: WO2013/024324
PCT Pub. Date: Feb. 21, 2013

(65) Prior Publication Data
US 2014/0206653 A1 Jul. 24, 2014

(51) Int. Cl.
*A61K 31/66* (2006.01)
*C07F 1/08* (2006.01)
*A61K 33/34* (2006.01)

(52) U.S. Cl.
CPC ............... *A61K 31/66* (2013.01); *A61K 33/34* (2013.01)

(58) Field of Classification Search
CPC ........... C07F 1/08; A61K 31/66; A61K 33/24
USPC ............................................ 556/21; 514/499
See application file for complete search history.

(56) References Cited

FOREIGN PATENT DOCUMENTS

IT 1369596 B1 * 1/2010

OTHER PUBLICATIONS

Santini, C., et al., "In Vitro Anntitumor Activity of Water Soluble Cu(I), Ag (I) and Au (I) Complexes Supported by Hydrophilic Alkyl Phosphine Ligands", Journal of Inorganic Biochemistry, 2011,105: 232-240.
Database CA (Online) Chemical Abstract Service, Columbus, Ohion, US; Gioia Lobbia, Giancarlo, et al., "Copper hydromethylphosphinate complexes and their use as antitumor agents", XP002663867, retrived from STN Database Accession No. 2009:1576228, IT 2006 MCO 059 A1 (Associazione Dream MC, Italy; Fondazione Cassa Di Risparmio Della Prov) Aug. 16, 2006.
Hydroxmethylphosphine Cu(I) complexes and their use as antitumor agents ( EnglishTranslation of IT 2006 MCO 059 A1).
Marzano, C., et al, "In Vitro Antitumor Activity of the Water Soluble Copper (I) Complexes Bearing the Tris (hydroxymethyl)phosphine Ligand", Journal of medicinal Chemistry, 2008,51; 798-808.
Bettio Frazia: "Complessi metallici come agenti antitumorali: identificazione di nuovi target cellulari e subcelluari", 2007, XP002663869, Retrieved from the internet: URL: http://www.ciromsb.uniba.it/relazioni% 20borsisti/2007/Nuovi% 20Farmaci/Bettio.pdf [retrieved on Nov. 17, 2011].
Bettio Frazia: Metal "Complexes as anticancer agents: identification of novel cellular and subcellular targets", Final Report:"CIRCMSB Fellowship" Tutor: Dr. Cristina Marzano (English Translation of Bettio Frazia).
Bettio, F., "Complessi metallici come agenti antitumorali: identificazione di nuovi target cellulari e subcelluari", "Relazioni sulle ricerche svolte dagli assegnatari di Borsa di Studio del C.I.R.C.M.S.B.—Anno 2007" , 2007, XP002663870, Retrieved from the Internet:URL:http://www.circmsb.uniba.it/ [retrieved on Nov. 17, 2011].
Bettio, F., "Metal Complexes as Potential Antitumor Agents: Identification of New Cellular and Subcellular Targets","Report on researches Developed by C.I.R.C.M.S.B. Fellowship Students—2007" (English Translation of Bettio, F).
Tisato, F., et al., "The Relationship between the electrospray ionization behaviour and biological activity of some phosphino Cu(I) complexes", Rapid Communications in Mass Spectrometry, 2010, 24; 1610-1616.
Gandin, V., et al., "A Novel Copper Complex Induces Paraptosis in Colon Cancer Cells via the Activation of ER Stress Signalling", Journal of Cellular and Molecular Medicine, 2012, 16 (1);142-151.

* cited by examiner

*Primary Examiner* — Porfirio Nazario Gonzalez
(74) *Attorney, Agent, or Firm* — Francis J. Tinney (57) ABSTRACT

Cu(I) complexes of the type $[Cu(thp)4]_n[X]_{-n}$, wherein thp is a tris(hydroxymethyl)phosphine, X is a counteranion, n=1-4, for the use as antineoplistic agents against solid tumors in humans.

4 Claims, 2 Drawing Sheets

[CU(THP)4]N[X]-N COMPOUNDS FOR THE TREATMENT OF A BROAD RANGE OF HUMAN SOLID TUMORS, INCLUDING REFRACTORY TUMORS

This application is a 35 USC 371 application of PCT/IB2011/053624 filed on Aug. 16, 2011, which is incorporated herein by reference in its entirety.

TECHNICAL FIELD OF INVENTION

The invention concerns hydrophilic copper(I) complexes of the type $[Cu(thp)_4]_n[X]_{-n}$ used as antitumor agents toward a broad range of solid tumors, including refractory tumors, in humans.

BACKGROUND OF INVENTION

Cancer is a leading cause of death worldwide accounting for 7.4 million deaths (around 13% of all deaths) in 2004 according to data of World Health Organization (WHO).

The main types of cancer leading to overall cancer mortality each year are: lung (1.3 million deaths/year), stomach (803000 deaths), colorectal (639000 deaths) and liver (610000 deaths).

Deaths from cancer worldwide are projected to continue rising, with an estimated 12 million deaths in 2030.

Some of the most common cancer types, such as breast cancer, cervical cancer and colorectal cancer, have high cure rates when detected early and treated according to best practice, but others still require continuous research to reach acceptable cure rates. Principal treatment methods to cure tumors are surgery, radiotherapy and chemotherapy.

Chemotherapy includes treatment, among others, with metal-based drugs such as cis-diamminodichloro platinum (II) (CDDP) and other platinum(II) drugs such as carboplatin and oxaliplatin (OXP).

CDDP is approved by the Food and Drug Administration (FDA) to be used by itself to treat: i) bladder cancer that cannot be treated with surgery or radiotherapy and ii) ovarian cancer that has metastasized and has not gotten better with other drugs. In addition, CDDP is approved to be used in combination with other drugs to treat: i) advanced and metastatic ovarian cancer and ii) testicular cancer.

The second generation platinum(II) drug OXP is FDA approved for adjuvant therapy for stage III colorectal cancer and for initial therapy of advanced colorectal cancer.

Although highly effective in treating a variety of cancers, the use of platinum(II) drugs is limited by several side effects including nephrotoxicity, emetogenesis and neurotoxicity, and the emerging of inherited and/or acquired resistance phenomena.

Ongoing from the first generation drug CDDP to second generation carboplatin and OXP compounds, the issues of reducing toxicity over normal cells and to widen the spectrum of action toward additional human cancers have been only partially addressed.

Moreover, platinum drugs are often endowed with poor water solubility. A long-standing need exists for metallodrugs having improved hydrophilic character to get a suitable solubility in physiological conditions. In the search of new therapies avoiding these drawbacks, other metals have been considered as alternatives to platinum. Complexes including iron, cobalt and gold have shown promising results in pre-clinical studies, whereas complexes with titanium, ruthenium and gallium have already been evaluated in phase I and phase II clinical trials, as reviewed by I. Ott and R. Gust, Arch. Pharm. Chem. Life Sci., 2007, 340, 117-126. Metal complexes may undergo both redox reactions and ligand substitution, which allow them to participate in a variety of biological redox chemistries and to interact with different biological substrates.

In this perspective, even more challenging is the use of essential metal ions, such as copper (Cu). Since copper, as essential metal which escapes its normal metabolic pathways can be toxic to the organism, copper complexes may have the potential to be effective cytotoxic agents.

The approach of using copper complexes as antitumor agents, mimicking the widespread clinical use of platinum metallodrugs, has extensively been investigated.

The chemical identity, number and geometry of the ligating groups determine the relative stabilities of the resulting Cu(I) and Cu(II) complexes.

Analysis of small-molecule copper chemistry generally indicates that Cu(I) binding is thermodynamically favored by the inclusion of more sulfur, phosphorus and $sp^2$-nitrogen donors. As opposed, oxygen or $sp^3$-nitrogen donors stabilize Cu(II) species. Easy accessibility of two-, three- and four-coordinate geometries is another feature typical of Cu(I), whereas Cu(II) is better stabilized in four-, five- and six-coordinated arrangements, as reviewed by C. Marzano, M. Pellei, F. Tisato and C. Santini, Anti-Cancer Agents in Medicinal Chemistry, 2009, 9, 185-211 and by F. Tisato, C. Marzano, M. Porchia, M. Pellei and C. Santini, Medicinal Research Reviews, 2010, 30, 708-749.

The choice of using copper complexes offers the opportunity to make use of a more physiological metal with the interesting perspective of adopting cytotoxic mechanisms of action different from those exhibited by CDDP, in order to widen the spectrum of antitumor activity and contemporarily reduce toxic side effects. However, although a large assortment of cytotoxic copper compounds has been proposed as antiproliferative agents, only few compounds showed the desired characteristics to be evaluated as possible antitumor agents. Among such compounds, bis(aryl)diphosphine (P—P) metal(I) complexes of the type $[M(P-P)_2][Cl]$ wherein M can be gold (Au), silver (Ag) or copper (Cu) and P—P can be 1,2-bis(diphenylphosphine)ethane (dppe), 1,2-bis(diphenylphosphine)propane (dppp), 1,2-bis(diphenylphosphine)ethylene (dppey), showed cytotoxic activity in vitro against P388 murine leukemia (S. J. Berners-Price, C. K. Mirabelli, R. K. Johnson, M. R. Mattern, F. L. McCabe, L. F. Faucette, C. M. Sung, S. M. Mong, P. J. Sadler and S. T. Crooke, Cancer Res., 1986, 46, 5486-5493), B16 melanoma and M5076 reticulum cell sarcoma.

However, the presence of several phenyl groups appended to the phosphorus donors in bis(aryl)diphosphine gold and isostructural copper compounds caused undesired nephrotoxicity (S. J. Berners-Price, R. K. Johnson, C. K. Mirabelli, L. F. Faucette, F. L. McCabe and P. J. Sadler, Inorg. Chem., 1987, 26, 3383-3387) and cardiovascular toxicity (G. D. Hoke, R. A. Macia, P. C. Meunier, P. J. Bugelski, C. K. Mirabelli, G. F. Rush and W. D. Matthews, Toxicol. Appl. Pharmacol., 1989, 100, 293-306) in animal models, respectively, thus precluding clinical trials in humans.

Consequently, efforts have been devoted to the design of less lipophilic copper derivatives, as in the case of the partial substitution of the 'CuP$_4$' aryldiphosphine coordination sphere with heterocyclic thiones (M. K. Adwankar, C. Wycliff and A. Samuelson, Indian. J. Exp. Biol., 1997, 35, 810-814), acetonitrile (N. J. Sanghamitra, P. Phatak, S. Das, A. G. Samuelson and K. Somasundaram, J. Med. Chem., 2005, 48, 977-985), and N-heterocycles such as carbazole and benzotriazole producing mixed-ligand type compounds.

Following a similar mixed-ligand approach, several scorpionate ligands attached to a 'CuP$_2$' moiety, as disclosed by C. Marzano, M. Pellei, S. Alidori, A. Brossa, G. Gioia Lobbia, F. Tisato and C. Santini, J. Inorg. Biochem., 2006, 100, 299-304, wherein P$_2$ is bidentate dppe or two monodentate arylphosphine, have been tested.

The use of dihydrobis(3-nitro-1,2,4-triazolyl)borate scorpionate ligands, [H$_2$B (tz$^{NO2}$)$_2$], had the double aim at increasing the water solubility and the kinetic inertness of the resulting mixed-complexes. Chemosensitivity tests performed on CDDP sensitive and resistant human cancer cell lines established that [(scorpionate)Cu(thp)$_2$] type compounds were able to overcome CDDP resistance, supporting the hypothesis of a different mechanism of action compared to that exhibited by the reference drug CDDP. In particular, the compound [HC(CO$_2$)(pz$^{Me2}$)$_2$]Cu[P(CH$_2$OH)$_3$]$_2$ has demonstrated a significant antitumor activity in vitro, being active also against CDDP resistant cell lines.

However, this kind of mixed-ligand copper complexes is very difficult to synthesize and purify, and its cytotoxic potency is rather scarce.

The Italian Patent No. IT 1369596, which disclosure is herewith incorporated under reference, discloses copper(I) complexes with the ligand tris(hydroxymethyl)phosphine that confers an advantageous hydrophilic property to the corresponding Cu(I) compounds.

In the present invention, it is disclosed the use of hydrophilic phosphino Cu(I) complexes instead of lipophilic ones in order to avoid the toxicity problems. The hydrophilic feature is given by the choice of the hydrophilic tris(hydroxymethyl)phosphine (thp) ligand, which allows the preparation of perfectly aqueous soluble species (C. Marzano, M. Pellei, D. Colavito, S. Alidori, G. Gioia Lobbia, V. Gandin, F. Tisato and C. Santini, J. Med. Chem., 2006, 49, 7317-7324).

Advantages of the Invention

The above discussed problems and deficiencies of the prior art are overcome or alleviated by the invention which provides hydrophilic copper(I) complexes of the type [Cu(thp)$_4$]$_n$[X]$_{-n}$ as antitumor agents toward a broad range of human solid tumors, including refractory solid tumors.

In hydrophilic copper(I) complexes of the type [Cu(thp)$_4$]$_n$[X]$_{-n}$, X comprises N$_3$ (azide), PF$_6$, NO$_3$, NO$_2$, ClO$_4$, Cl, Br, I, C$_6$H$_{11}$(CH$_2$)$_3$CO$_2$ (cyclohexanebutyrate), D-gluconate, CH$_3$COO, CF$_3$COO, HCOO, C$_5$HF$_6$O$_2$ (hexafluoroacetylacetonate), C$_5$H$_4$F$_3$O$_2$ (trifluoroacetylacetonate), BF$_4$, CF$_3$SO$_3$, BH$_4$, HBpz$_3$ (pyrazolylborates), HBtz$_3$ (triazolylborates), CH$_3$(CH$_2$)$_{11}$OSO$_3$ (dodecylsulfate), C$_4$H$_9$(C$_2$H$_5$)CHCOO (2-ethylexanoate), B(C$_2$H$_5$)$_4$ (tetraethylborate), C$_{17}$H$_{35}$COO (stearate), B(C$_6$H$_5$)$_4$ (tetraphenylborate), BH(CH$_3$COO)$_3$ (triacetoxyborohydride), CB$_{11}$H$_6$Br$_6$ (exabromocarborane), C$_{10}$H$_{19}$O$_2$ (neodecanoate), SCN (thiocyanate), C$_{11}$H$_{19}$O$_2$ (TMHD) for n=1, X comprises PO$_3$F (fluorophosphate), SiF$_6$ (hexafluorosilicate), C$_2$O$_4$ (oxalate), SeO$_3$ (selenite), S (sulfide), SO$_3$ (sulfite), B$_4$O$_2$, SiO$_3$ (metasilicate), HPO$_4$, CO$_3$, SO$_4$ for n=2, X comprises PO$_4$ for n=3, X comprises SiO$_4$ (ortosilicate) for n=4.

[Cu(thp)$_4$]$_n$[X]$_{-n}$ complexes are stable toward disproportionation to Cu(II) and Cu$^\circ$ in aqueous media, a property which was elusive for decades for Cu(I) compounds. Contemporary, [Cu(thp)$_4$]$_n$[X]$_{-n}$ complexes exhibit unexpected lability with sequential loss of one, two or three phosphines at micromolar concentration, that is the concentration at which copper compounds display their antitumor activity. This peculiar combination of thermodynamic stability and kinetic lability is essential for establishing the interaction of the metal with the biological substrate to promote cytotoxicity toward cancer cells. The use of mono-dentate phosphines such as thp in [Cu(thp)$_4$]$_n$[X]$_{-n}$ compounds therefore grants superior antitumor efficacy compared to the use of bidentate phosphines reported in a previous japanese patent (WO2007066557 by K. Hiroaki; O. Keisuke; O. Nobuhiko; N. Kazuhiro; K. Yoshirou).

Most of the in vitro studies and all of the in vivo studies have been performed with the representative [Cu(thp)$_4$][PF$_6$] complex (also indicated with CP throughout the text). However, our investigations indicate that any [X] counteranion comprised in the [Cu(thp)$_4$]$_n$[X]$_{-n}$ formulation can be used in the biological test without affecting the cytotoxic potency of the drug. The counteranion [X] therefore acts as a mere ancillary group of the [Cu(thp)$_4$]$^+$ cation, that is the genuine active ingredient of the metallodrug.

BRIEF DESCRIPTION OF THE FIGURES

Further advantages of the use of hydrophilic copper(I) complexes of the type [Cu(thp)$_4$]$_n$[X]$_{-n}$ as antitumor agents toward a broad range of human solid tumors, including refractory solid tumors, will be appreciated and understood by those skilled in the art from the following detailed description and drawings, shown for exemplificative and not limitative purposes, wherein.

DETAILED DESCRIPTION OF THE INVENTION

In discussing tumors, i.e. collections of abnormally growing cells that are malignant (or cancerous) the term "solid tumor" is intended as a localized mass of tissue.

Solid tumors are distinguished from leukemia, actually a type of tumor that takes on the fluid properties of the organ, in this case affecting the blood.

Different kinds of solid tumors are named depending on the type of cells of which they are composed as:
a) sarcomas arising from connective or supporting tissues such as bone or muscle,
b) carcinomas arising from the body's glandular cells and epithelial cells,
c) lymphomas, cancers of the lymphoid organs such as the lymphnodes, spleen, and thymus, which produce and store infection-fighting cells. These cells also occur in almost all tissues of the body, and lymphomas therefore may develop in a wide variety of organs.

Copper is an essential trace element in all organisms living in oxygen-rich environments. Copper homeostasis is therefore tightly regulated by both transcriptional control and selective transport mechanisms through a conserved group of proteins.

When copper escapes its normal metabolic pathways it can be toxic to the organism. In this situation it may become a potential cytotoxic agent, as disclosed by J. J. R. Fausto Da Silva and R. J. P. Williams, The Biological Chemistry of the Elements: The Inorganic Chemistry of Life Oxford University Press, New York, 1991.

In the field of metal-based antitumour drugs, the present invention discloses the use of copper compounds as antitumor agents instead of conventional clinically used platinum(II)-based drugs.

In any drug discovery program, tumor response to a new candidate antineoplastic agent has to be validated by in vivo studies.

There are series of reports in literature describing poor correlation between in vitro cytotoxic activity and in vivo antitumor activity. In particular, in solid tumors, the reasons for the lack of in vitro/in vivo correlation of drug activity are multifold and include permeability to the tumor cells, interstitial hypertension and metabolic degradation. For the effective treatment of solid tumors, anticancer drugs must gain access to all viable cells within the tumor mass in sufficient concentration to cause lethality. The effective treatment of solid tumors needs the drugs to penetrate several layers of tissue. On the other hand, antitumor drugs besides reaching tumor mass at adequate cytotoxic concentration, has to provoke minimal general tissue toxicity thus showing maximum cytotoxic selectivity against cancer cells.

Copper compounds according to the present invention are hydrophilic copper(I) complexes of the type $[Cu(thp)_4]_n[X]_{-n}$, wherein thp is a tris(hydroxymethyl)phosphine and X is $N_3$ (azide), $PF_6$, $NO_3$, $NO_2$, $ClO_4$, Cl, Br, I, $C_6H_{11}(CH_2)_3CO_2$ (cyclohexanebutyrate), D-gluconate, $CH_3COO$, $CF_3COO$, HCOO, $C_5HF_6O_2$ (hexafluoroacetylacetonate), $C_5H_4F_3O_2$ (trifluoroacetylacetonate), $BF_4$, $CF_3SO_3$, $BH_4$, $HBpz_3$ (pyrazolylborates), $HBtz_3$ (triazolylborates), $CH_3(CH_2)_{11}OSO_3$ (dodecylsulfate), $C_4H_9(C_2H_5)CHCOO$ (2-ethylexanoate), $B(C_2H_5)_4$ (tetraethylborate), $C_{12}H_{35}CO$ (stearate), $B(C_6H_5)_4$ (tetraphenylborate), $BH(CH_3COO)_3$ (triacetoxyborohydride), $CB_{11}H_6Br_6$ (exabromocarborane), $C_{10}H_{19}O_2$ (neodecanoate), SCN (thiocyanate), $C_{11}H_{19}O_2$ (TMHD) for n=1, X comprises $PO_3F$ (fluorophosphate), $SiF_6$ (hexafluorosilicate), $C_2O_4$ (oxalate), $SeO_3$ (selenite), S (sulfide), $SO_3$ (sulfite), $B_4O_7$, $SiO_3$ (metasilicate), $HPO_4$, $CO_3$, $SO_4$ for n=2, X comprises $PO_4$ for n=3, X comprises $SiO_4$ (ortosilicate) for n=4.

As better explained below, this kind of complexes shows antitumor activity demonstrated by both in vitro and in vivo investigations.

The molecular structure of hydrophilic copper(I) complexes of the type $[Cu(thp)_4]_n[X]_{-n}$ is:

These compounds have a tetrahedral geometry, with the four tris(hydroxymethyl)phosphine groups directly bonded to the copper center. The group indicated with X acts as counteranion.

These complexes are very easy to be synthesized, as disclosed in the Italian patent No. IT1369596 for two examples of hydrophilic copper(I) complexes of the type $[Cu(thp)_4]_n[X]_{-n}$, wherein X is $PF_6$ or $NO_3$.

The hydrophilic copper(I) complexes of the type $[Cu(thp)_4]_n[X]_{-n}$ are water soluble. The water solubility enhances the bioavailability and reduces the in vivo toxicity of these complexes. In particular, hydrophilic copper(I) complexes of the type $[Cu(thp)_4]_n[X]_{-n}$ show remarkable thermodynamic stability toward disproportionation to Cu(II) and Cu(0) in aqueous media. They are therefore much easier to manipulate in any biological test.

In mammalian, it is generally accepted that physiological copper is internalized into the cell as Cu(I), assumption based on the results obtained by competitive studies with monovalent and di-valent cations. On this basis, although copper (VII) red-ox chemistry is an active machinery in living systems, the possibility to deliver directly copper(I) species to the cell membrane may help cellular internalization of the metal, thereby enhancing its biological activity.

Hydrophilic copper (I) complexes of the type $[Cu(thp)_4]_n[X]_{-n}$ exhibit unexpected kinetic lability with sequential loss of phosphines thereby allowing the efficient interaction of the metal with the biological substrate to promote cancer cell cytotoxicity.

In fact, hydrophilic copper(I) complexes of the type $[Cu(thp)_4]_n[X]_{-n}$, with improved pharmacological properties, are proposed as effective agents against solid tumors in humans, including refractory solid tumors, in particular those that express both inherited and acquired resistance to platinum(II) drugs. Both in vitro and in vivo results confirm the antitumor activity of these complexes in solid tumors in humans.

Solid tumors comprises cancers of lung, colon, pancreas, stomach, liver, oesophagus, gastric cardia, bone, brain, skin, breast, urogenital tract, including ovary, cervix and prostate, etc.

Treatment with the hydrophilic copper(I) complexes of the type $[Cu(thp)_4]_n[X]_{-n}$ of human cancer cells derived from solid tumors allows to obtain an important cytotoxic effect with a drug dose significantly lower than traditional platinum (II) drugs.

The cytotoxic activity of hydrophilic copper(I) complexes of the type $[Cu(thp)_4]_n[X]_{-n}$ in human cancer cell lines derived from solid tumours is shown in Table 1 below.

The in vivo inhibition of solid tumor growth, index of the cytotoxic activity of hydrophilic copper(I) complexes of the type $[Cu(thp)_4]_n[X]_{-n}$, is shown for early-stage tumor treatment in Table 7 below, for advanced-stage tumor treatment (1) in Table 8 below and for advanced-stage tumor treatment (2) in Table 9 below.

Hydrophilic copper(I) complexes of the type $[Cu(thp)_4]_n[X]_{-n}$ are, from in vitro data, in the average 50-fold more cytotoxic than CDDP and OXP.

Moreover, data obtained from the in vitro antitumor studies provide evidence that hydrophilic copper(I) complexes of the type $[Cu(thp)_4]_n[X]_{-n}$ have anticancer activity also in CDDP and OXP resistant cancers. The antitumor activity of hydrophilic copper(I) complexes of the type $[Cu(thp)_4]_n[X]_{-n}$ towards sensitive and resistant cell lines derived from human solid tumors is shown in Table 2 below. The hydrophilic copper(I) complexes of the type $[Cu(thp)_4]_n[X]_{-n}$, display antitumor activity levels very similar on both sensitive and resistant cell lines derived from human solid tumors, indicating different cross-resistance profiles than those of traditional platinum-drugs. The cytotoxic activity towards drug resistant solid tumors makes hydrophilic copper(I) complexes of the type $[Cu(thp)_4]_n[X]_{-n}$ suitable antitumor agents for the treatment of refractory solid tumors.

In vitro data confirm a noticeable preferential cytotoxicity of hydrophilic copper(I) complexes of the type $[Cu(thp)_4]_n[X]_{-n}$ versus neoplastic cells. Hydrophilic copper(I) complexes of the type $[Cu(thp)_4]_n[X]_{-n}$ have, therefore, a selective tumor cell killing effect, as shown in Tables 3 and 4 below.

Figure 2:
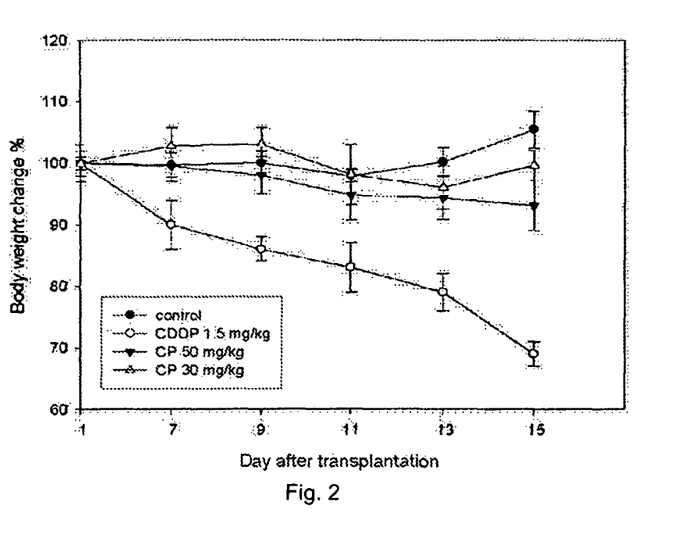
FIG. 2 shows a chart of body weight changes in advanced-stage treatment (1) of LLC-bearing C57BL mice treated with vehicle or tested compounds. Body weight was measured at day 1 and every two days from day 7 and was taken as a parameter of systemic toxicity. The X axis indicates the days after transplantation whereas the Y axis indicates the percentage of body weight changes. Black circle line is the control, white circle line indicates the treatment with 1.5 mg/kg of CDDP, black triangle line indicates the treatment with 50 mg/kg of CP, and white triangle line indicates the treatment with 30 mg/kg of CP. The error bars indicate the SD.
Figure 3:
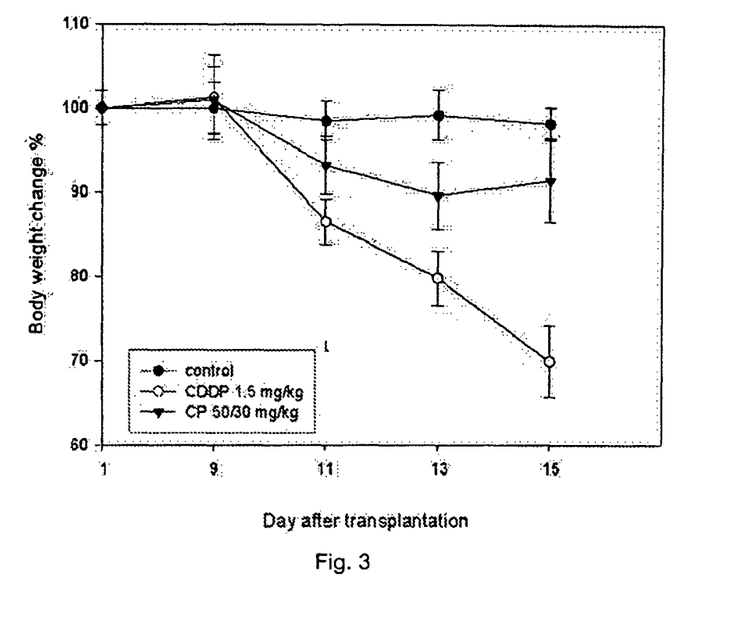
FIG. 3 shows a chart of body weight changes in advanced-stage treatment (2) of LLC-bearing C57BL mice treated with vehicle or tested compounds. Body weight was measured at day 1 and every two days from day 9 and was taken as a parameter of systemic toxicity. The X axis indicates the days after transplantation whereas the Y axis indicates the percentage of body weight changes. Black circle line is the control, white circle line indicates the treatment with 1.5 mg/kg of CDDP, and black triangle line indicates the treatment with 50/30 mg/kg of CP. The error bars indicate the SD.

In vivo data concerning toxicity tests demonstrate that hydrophilic copper(I) complexes of the type $[Cu(thp)_4]_n[X]_{-n}$ have reduced toxicity versus normal cells, without adverse effects nor anorexia. These data are shown in Tables 5 and 6 below and in FIGS. 1-3.

The Applicant, in the present invention, has demonstrated that the use of hydrophilic copper(I) complexes of the type $[Cu(thp)_4]_n[X]_{-n}$ is highly effective, selective and safe in solid tumor therapy, wherein such complexes are used as effective antineoplastic agents. Hydrophilic copper(I) complexes of the type $[Cu(thp)_4]_n[X]_{-n}$ display, moreover, mechanism of action, biodistribution and toxicity which are different from those of currently used platinum drugs.

The hydrophilic copper(I) complexes of the type $[Cu(thp)_4]_n[X]_{-n}$ can be administered, in the treatment of solid tumors in humans, in aqueous solution taking advantage of their excellent solubility in water or they can be administered orally, subcutaneously or parenterally.

In a version of the invention, in the hydrophilic copper(I) complexes of the type $[Cu(thp)_4]_n[X]_{-n}$, X is $PF_6^-$. $[Cu(thp)_4][PF_6]$ (also indicated as CP) is a hydrophilic copper (I) complex and displays high in vitro and in vivo antitumor activity. Preliminary in vitro data referring to CP have been disclosed by C. Mariano, V. Gandin, M. Pellei, D. Colavito, G. Papini, G. Gioia Lobbia, E. Del Giudice, M. Porchia, F. Tisato and C. Santini, J. Med. Chem., 2008, 51, 798-808.

In an embodiment of the present invention, CP is used as antineoplastic agent in the treatment of solid tumors in humans, including refractory solid tumors expressing both inherited and acquired resistance to platinum(II) drugs.

Methods indicated in the below description and examples have explicative and not limitative value.

As indicated from values of Table 5, CP is particularly desirable because it has reduced toxicity in vivo. In fact, the median lethal doses ($LD_{50}$) calculated for CP is about one order of magnitude higher than that recorded with CDDP.

As explained in Example VI, the toxicity profile of CP has been determined by means of acute and repeated-dose toxicity studies in BALB/c and C57BL mice. CDDP was used as reference compound. The acute toxicity was assessed by treating BALB/c or C57BL mice with a single intraperitoneal (i.p.) or endovenous (e.v.) administration of different amounts, i.e. 3.125, 6.25, 12.5, 25, 50, 100 and 200 mg/kg of tested compounds. The animals were observed for 24 hrs for signs of toxicity and mortality.

Furthermore, as indicated from values of Table 6, the administration of CP was markedly better tolerated by mice than traditional metallodrugs.

Figure 1:
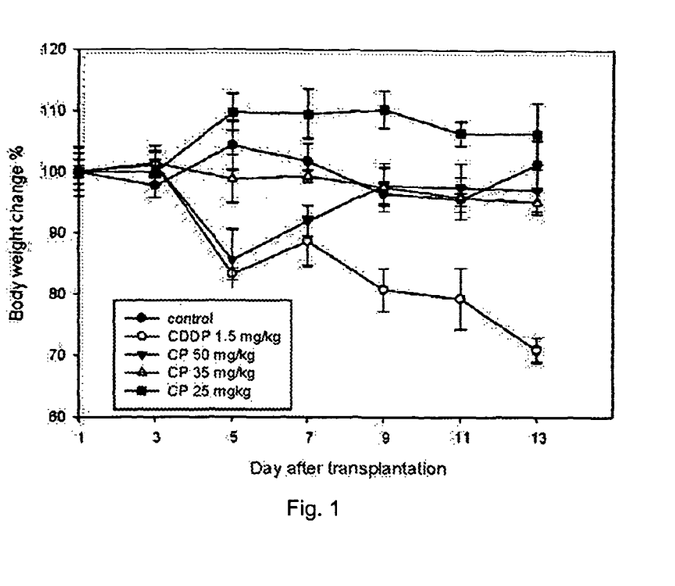
FIG. 1 shows a chart of body weight changes in early-stage treatment of LLC-bearing C57BL mice treated with vehicle or tested compounds. Body weight was measured every two days and was taken as a parameter of systemic toxicity. The X axis indicates the days after transplantation whereas the Y axis indicates the percentage of body weight changes. Black circle line is the control, white circle line indicates the treatment with 1.5 mg/kg of CDDP, black triangle line indicates the treatment with 50 mg/kg of CP, white triangle line indicates the treatment with 35 mg/kg of CP, and square line indicates the treatment with 25 mg/kg of CP. The error bars indicate the SD.

The antitumor efficacy of CP was evaluated in a model of solid tumor, the syngeneic murine Lewis Lung Carcinoma (also indicated as LLC). CP has been administered in aqueous solution taking advantage of its excellent solubility in water. As indicated in Table 7, CP treatment of early stage LLC resulted in a dose-dependent inhibition of proliferation of tumor cell population in vivo. CP exerted a statistically significant antitumor activity compared to vehicle-treated mice, even at the lower daily dose of 25 mg/kg with a tumor growth inhibition of 26%. Mice treated with 50 mg/kg of CP showed a tumor growth inhibition slightly higher to that observed for mice treated with 1.5 mg/kg of CDDP. Body weight of tumor-bearing mice has been measured every two days simultaneously with antitumor analyses and was taken as a parameter of systemic toxicity. As shown in FIG. 1, the mice treated with CP, even at the highest doses, showed no significant body weight loss when compared with the non-treated group on the same day. In contrast, the mice treated with CDDP showed about 30% of body weight loss after the sixth administration resulting, as expected, from CDDP toxicity.

Mice treated with advanced-stage treatment (2) schedule, consisting of a higher loading dose of 50 mg/kg followed by a low maintenance dose of 30 mg/kg of CP, as indicated in Table 9, showed a quite complete tumor regression after the sixth administration. The complete disappearance of primary tumors in these mice was confirmed by dissection on day 15.

Differently, CDDP dosed at 1.5 mg/kg induced a tumor regression of 72%. The time course of body weight changes, depicted in FIGS. 2 and 3, indicates that treatment with CP did not induce any adverse effects including significant body weight loss throughout the therapeutic experiment. Mice treated with CP showed no clinical signs of toxicity and no anorexia, whereas those treated with CDDP appeared prostrate and showed substantial weight loss.

Therefore, in a murine solid tumor model, CP and more generally hydrophilic copper(I) complexes of the type $[Cu(thp)_4]_n[X]_{-n}$ led to a complete tumor regression without any appreciable clinical sign of toxicity. To assess the potential selectivity to the solid tumor mass, tissue distribution of CP was investigated in LLC bearing C57BL mice. Biodistribution studies are very helpful in assessing the ability of a molecule to traverse multilayers of cells. Chemotherapy of solid tumors often fails because adequate cytotoxic concentrations are not achieved due to poor penetration and non-uniform distribution of the drug. As outlined in FIG. 4, the examination of CP biodistribution characteristics demonstrated that CP achieved significant and selective accumulation within the solid tumor mass. No copper drug was detected in brain and very little was found in the intestinal tract. The solid tumor mass presented the highest CP concentration, followed by spleen, kidney, liver and stomach.

This feature confirms cytotoxicity data and preliminary uptake studies on cancer cells suggesting that the intracellular accumulation of CP is mediated by the endogenous transmembrane copper carrier hCtr1, that recently has been found overexpressed in many types of human solid tumors i.e. prostate and colon cancers.

On the other hand, CP has demonstrated high cytotoxicity against several human leukemic cell lines but failed to show significant antitumor efficacy against established animal leukaemia. These results, once again, point out the need of in vivo investigations in assessing the antitumor efficacy of putative anticancer agents. The detection of drug uptake by tumor cells in animal models clearly attest that CP efficiently and selectively accumulates in the solid tumor mass.

All these findings confirm that CP, and more generally hydrophilic copper(I) complexes of the type $[Cu(thp)_4]_n[X]_{-n}$, act as highly effective and selective antitumor agents for solid tumor therapy.

Previous studies describing the biological effects in cancer cells by $[Cu(thp)_4]_n[X]_{-n}$ revealed the triggering of a non-apoptotic programmed cell death (PCD) defined as paraptosis (type III B cell death) likely due to the inhibition of proteolytic activities of 26S proteasome.

The induction of an alternative PCD other than apoptosis, indeed, represents a valuable therapeutic strategy to overcome drug resistance, which is frequently related to a compromised capacity of cancer cells to trigger the apoptotic process.

Therefore, in the present invention hydrophilic copper(I) complexes of the type $[Cu(thp)_4]_n[X]_{-n}$ are proposed as innovative metal-based antitumor drugs for the therapy of a broad range of solid tumors, including refractory solid tumors in humans.

Cu(I) complexes of the type $[Cu(thp)_4]_n[X]_{-n}$ according to the present invention are in the form suitable for the administration to humans in the treatment of solid tumors and/or refractory solid tumors. The suitable form for administration is in aqueous solution or in an oral formulation or in a subcutaneously or parenterally administrable form.

The present invention presents a pharmaceutical composition comprising Cu(I) complexes of the type $[Cu(thp)_4]_n[X]_{-n}$, wherein thp is a tris(hydroxymethyl)phosphine and X is $N_3$ (azide), $PF_6$, $NO_3$, $NO_2$, $ClO_4$, Cl, Br, I, $C_6H_{11}(CH_2)_3CO_2$ (cyclohexanebutyrate), D-gluconate, $CH_3COO$, $CF_3COO$, $HCOO$, $C_5HF_6O_2$ (hexafluoroacetylacetonate), $C_5H_4F_3O_2$ (trifluoroacetylacetonate), $BF_4$, $CF_3SO_3$, $BH_4$, $HBpz_3$ (pyrazolylborates), $HBtz_3$ (triazolylborates), $CH_3(CH_2)_{11}OSO_3$ (dodecylsulfate), $C_4H_9(C_2H_5)CHCOO$ (2-ethylexanoate), $B(C_2H_5)_4$ (tetraethylborate), $C_{17}H_{35}COO$ (stearate), $B(C_6H_5)_4$ (tetraphenylborate), $BH(CH_3COO)_3$ (triacetoxyborohydride), $CB_{11}H_6Br_6$ (exabromocarborane), $C_{10}H_{19}O_2$ (neodecanoate), SCN (thiocyanate), $C_{11}H_{19}O_2$ (TMHD) for n=1, X comprises $PO_3F$ (fluorophosphate), $SiF_6$ (hexafluorosilicate), $C_2O_4$ (oxalate), $SeO_3$ (selenite), S (sulfide), $SO_3$ (sulfite), $B_4O_7$, $SiO_3$ (metasilicate), $HPO_4$, $CO_3$, $SO_4$ for n=2, X comprises $PO_4$ for n=3 and X comprises $SiO_4$ (ortosilicate) for n=4 for the treatment of solid tumors and/or refractory solid tumors in humans.

In a version of the invention, the pharmaceutical composition comprises $[Cu(thp)_4][PF_6]$ (also indicated as CP).

The pharmaceutical composition according to the present invention is administered in aqueous solution or orally or subcutaneously or parenterally.

The present invention discloses a method for the treatment of at least a solid tumor by means of administration at an effective dose of Cu(I) complexes of the type $[Cu(thp)_4]_n[X]_{-n}$, wherein thp is a tris(hydroxymethyl)phosphine and X is $N_3$ (azide), $PF_6$, $NO_3$, $NO_2$, $ClO_4$, Cl, Br, I, $C_6H_{11}(CH_2)_3CO_2$ (cyclohexanebutyrate), D-gluconate, $CH_3COO$, $CF_3COO$, $HCOO$, $C_5HF_6O_2$ (hexafluoroacetylacetonate), $C_5H_4F_3O_2$ (trifluoroacetylacetonate), $BF_4$, $CF_3SO_3$, $BH_4$, $HBpz_3$ (pyrazolylborates), $HBtz_3$ (triazolylborates), $CH_3(CH_2)_{11}OSO_3$ (dodecylsulfate), $C_4H_9(C_2H_5)CHCOO$ (2-ethylexanoate), $B(C_2H_5)_4$ (tetraethylborate), $C_{17}H_{35}COO$ (stearate), $B(C_6H_5)_4$ (tetraphenylborate), $BH(CH_3COO)_3$ (triacetoxyborohydride), $CB_{11}H_6Br_6$ (exabromocarborane), $C_{10}H_{19}O_2$ (neodecanoate), SCN (thiocyanate), $C_{11}H_{19}O_2$ (TMHD) for n=1, X comprises $PO_3F$ (fluorophosphate), $SiF_6$ (hexafluorosilicate), $C_2O_4$ (oxalate), $SeO_3$ (selenite), S (sulfide), $SO_3$ (sulfite), $B_4O_7$, $SiO_3$ (metasilicate), $HPO_4$, $CO_3$, $SO_4$ for n=2, X comprises $PO_4$ for n=3 and X comprises $SiO_4$ (ortosilicate) for n=4.

In a version of the method according to the present invention the Cu(I) complex of the type $[Cu(thp)_4]_n[X]_{-n}$ is $[Cu(thp)_4][PF_6]$ (also indicated as CP).

EXAMPLE I

In Vitro Antitumor Activity of $[Cu(thp)_4][PF_6]$ (Also Indicated as CP) Towards Several Human Cancer Cell Lines The in vitro antitumor activity of CP had been deeply evaluated in several human cancer cell lines by in vitro cytotoxicity assays. CP cytotoxicity has been detected in a large panel of human cell lines derived from a wide variety of solid tumors, including refractory tumors. In Table 1, the cytotoxicity parameters $IC_{50}$ (that is the median growth inhibitory concentrations calculated from dose-survival curves via MTT test) are tabulated.

Cell lines representative of lung (H157, U1810, U1285, Calu-1), pancreas (MIA PaCa-2, BxPC-3, AsPC-1, Capan-1), liver (Huh-7, Hep 3B, SK-Hep-1), oesophagus (OE33, OE21), oesophagus/gastric cardia (OE19), stomach (BGC-823, AGS), colon (HCT-116, T84, COLO 205), breast (MDA-MB-231, SK-BR-3), cervix (CaSki, C-33 A) ovarian (A2780, SK-OV-3, IGROV1), prostate (LnCaP, PC-3) cancers along with melanoma (MEWO, G361, C-32), neuroblastoma (SH-SY5Y, SK-N-AS, IMR-32) and osteosarcoma (U-2 OS, MG-63) have been treated with increasing concentration of CP for 72 hrs.

Cancer cell lines corresponded to different stages of disease progression and were endowed with different degree of sensitivity to CDDP or OXP.

For comparison purposes, cytotoxicity values of CDDP and OXP were assessed under the same experimental conditions.

TABLE 1

Cytotoxic activity of CP, CDDP and OXP in human cancer cell lines derived from solid tumors.

| Cell line | Tissue type | $IC_{50}$ (µM) ± S.D. | | |
|---|---|---|---|---|
| | | CP | CDDP | OXP |
| H157 | lung | 1.51 ± 0.66 | 5.99 ± 2.71 | 25.34 ± 0.52 |
| U1810 | lung | 0.76 ± 1.02 | 3.24 ± 1.92 | nd |
| U1285 | lung | 0.87 ± 0.51 | 4.37 ± 1.06 | nd |
| Calu-1 | lung | 0.91 ± 0.45 | 9.65 ± 2.13 | 4.23 ± 1.53 |

TABLE 1-continued

Cytotoxic activity of CP, CDDP and OXP in human cancer cell lines derived from solid tumors.

| | | $IC_{50}$ (µM) ± S.D. | | |
|---|---|---|---|---|
| Cell line | Tissue type | CP | CDDP | OXP |
| MIA PaCa-2 | pancreas | 2.45 ± 0.97 | 25.87 ± 2.75 | 16.76 ± 1.89 |
| BxPC-3 | pancreas | 1.34 ± 1.11 | 11.46 ± 2.51 | 4.15 ± 1.06 |
| AsPC-1 | pancreas | 1.55 ± 0.73 | 29.47 ± 1.57 | 23.21 ± 2.64 |
| Capan-1 | pancreas | 2.43 ± 0.84 | 9.81 ± 1.38 | 3.17 ± 0.97 |
| Huh-7 | liver | 0.76 ± 0.31 | 3.24 ± 0.96 | 1.12 ± 1.05 |
| Hep 3B | liver | 0.67 ± 0.47 | 6.15 ± 1.48 | 4.32 ± 1.33 |
| SK-Hep-1 | liver | 0.86 ± 0.75 | 27.12 ± 2.94 | 17.78 ± 2.63 |
| OE33 | oesophagus | 1.87 ± 0.59 | 6.87 ± 1.06 | nd |
| OE21 | oesophagus | 1.19 ± 0.72 | 3.76 ± 1.08 | nd |
| OE19 | Oesophagus/ gastric cardia | 1.66 ± 0.94 | 7.45 ± 1.37 | 8.76 ± 1.51 |
| BGC-823 | stomach | 1.08 ± 0.66 | 3.21 ± 1.00 | nd |
| AGS | stomach | 1.14 ± 0.78 | 6.33 ± 1.79 | 5.32 ± 1.63 |
| HCT-116 | colon | 0.46 ± 0.07 | 8.26 ± 1.11 | 0.76 ± 0.58 |
| T84 | colon | 0.24 ± 0.04 | 7.67 ± 1.34 | 0.33 ± 0.09 |
| COLO 205 | colon | 0.65 ± 0.03 | 33.11 ± 2.68 | 21.11 ± 2.66 |
| SH-SY5Y | brain | 0.66 ± 0.12 | 5.16 ± 1.23 | 4.43 ± 1.07 |
| SK-N-AS | brain | 0.94 ± 0.75 | 18.11 ± 1.58 | 19.24 ± 2.77 |
| IMR-32 | brain | 0.72 ± 0.18 | 4.45 ± 0.98 | 11.12 ± 2.97 |
| MEWO | skin | 1.13 ± 0.74 | 6.76 ± 1.47 | 6.43 ± 1.54 |
| G361 | skin | 0.98 ± 0.12 | 1.32 ± 1.01 | 1.14 ± 0.31 |
| C-32 | skin | 0.56 ± 0.43 | 1.06 ± 0.98 | 1.12 ± 0.42 |
| U-2 OS | bone | 1.34 ± 0.92 | 5.15 ± 1.94 | 0.72 ± 0.24 |
| MG-63 | bone | 1.43 ± 0.74 | 5.76 ± 1.01 | nd |
| MDA-MB-231 | breast | 2.11 ± 1.23 | 3.23 ± 1.56 | 4.35 ± 1.07 |
| SK-BR-3 | breast | 1.89 ± 0.99 | 5.12 ± 1.51 | 8.98 ± 2.64 |
| CaSki | cervix | 3.16 ± 1.45 | 31.13 ± 2.97 | 26.12 ± 3.01 |
| C-33 A | cervix | 3.26 ± 1.57 | 7.42 ± 1.98 | nd |
| A2780 | ovary | 0.99 ± 0.42 | 1.25 ± 1.01 | 0.55 ± 0.22 |
| SK-OV-3 | ovary | 0.88 ± 0.43 | 3.04 ± 0.95 | 1.43 ± 1.03 |
| IGROV1 | ovary | 0.91 ± 0.94 | 6.01 ± 1.73 | 2.56 ± 2.14 |
| LNCap | prostate | 0.65 ± 0.87 | 1.08 ± 1.01 | nd |
| PC-3 | prostate | 0.98 ± 0.97 | 1.57 ± 1.13 | 5.23 ± 1.62 |

The growth inhibitory effect was evaluated by means of MTT test. 5-8 × 10$^4$ mL$^{-1}$ cells (depending on the growth characteristics of the cell line) were treated for 72 hrs with increasing concentrations of tested compounds.
$IC_{50}$ values were calculated from the dose-survival curves by four parameter logistic model ($P < 0.05$).
SD = standard deviation,
nd = not detected.

All cancer cell lines of different histotypes, included in Table 1 showed a consistently good response toward CP treatment. In colon, liver, brain, ovary and prostate cell line panels $IC_{50}$ values in the submicromolar range have been obtained. On the whole, CP yielded $IC_{50}$ values ranging from less than 0.3 µM to 3 µM being up to 50- and 30-fold more cytotoxic than CDDP and OXP, respectively.

Anyway, for all the fourteen different histotypes, the average $IC_{50}$ values obtained with CP treatment were always lower than those obtained with CDDP and lower or at worst equal to those obtained after OXP treatment.

EXAMPLE II

In Vitro Antitumor Activity of [Cu(thp)$_4$][PF$_6$] (Also Indicated as CP) Towards Ovarian Adenocarcinoma and Osteosarcoma CDDP Resistant Cells and Colon Adenocarcinoma OXP Resistant Cells The tendency of malignant cells to acquire mutations that allow them to resist the effects of antineoplastic drugs is an important factor limiting the effectiveness of chemotherapy of solid tumors.

Table 2 shows cross-resistance profiles obtained testing CP in ovarian adenocarcinoma and osteosarcoma CDDP resistant cells and in colon adenocarcinoma OXP resistant cells. Resistant cell sublines have been suitably selected for their acquired drug resistance by treatment with increasing concentrations of platinum drugs.

CP displayed antitumor activity levels very similar on both sensitive and resistant cell lines indicating different cross-resistance profiles than those of CDDP and OXP.

CP treatment yielded $IC_{50}$ values up to 15-fold lower than the reference metallodrugs.

The calculation of the Resistant Factor (RF), which is defined as the ratio between $IC_{50}$ calculated for the resistant cells and those arising from the sensitive ones, indicated a striking lack of cross-resistance between CP and platinum drugs.

TABLE 2

CP, CDDP and OXP cross resistance profiles

| | $IC_{50}$ (µM) ± SD | | |
|---|---|---|---|
| | A2780 | A2780cisR | R.F. |
| CP | 1.8 ± 0.4 | 2.1 ± 1.2 | 1.2 |
| CDDP | 2.43 ± 1.6 | 13.1 ± 2.3 | 5.3 |

| | $IC_{50}$ (µM) ± SD | | |
|---|---|---|---|
| | U-2 OS | U-2 OS Pt | R.F. |
| CP | 3.1 ± 1.1 | 4.3 ± 1.1 | 0.2 |
| CDDP | 5.9 ± 1.4 | 14.6 ± 1.3 | 2.5 |

| | $IC_{50}$ (µM) ± SD | | |
|---|---|---|---|
| | HCT-116 | HCT-116 OXP | R.F. |
| CP | 1.4 ± 0.5 | 1.9 ± 0.7 | 1.4 |
| OXP | 1.2 ± 0.1 | 23.3 ± 1.0 | 19.4 |

CP was tested against human cancer cell lines suitably selected for their sensitivity and resistance to CDDP or OXP: human ovarian adenocarcinoma cells sensitive (A2780) and resistant (A2780cisR) to CDDP, human osteosarcoma cells sensitive (U-2 OS) and resistant (U-2 OS/Pt) to CDDP, human colon adenocarcinoma cells sensitive (HCT-116) and resistant (HCT-116 OXP) to OXP have been tested. For comparison purposes, the cytotoxicity of CDDP or OXP was assessed under the same experimental conditions.
The growth inhibitory effect was evaluated by means of MTT test. Cells (3-5 × 10$^4$ mL$^{-1}$, depending on the growth characteristics of the cell line) were treated for 72 h with increasing concentrations of tested compounds.
$IC_{50}$ values were calculated from the dose-survival curves by probit analysis ($P < 0.05$, $\chi^2$ test).
SD = standard deviation. Resistant factor (RF) is defined as $IC_{50}$ resistant/parent line.

EXAMPLE III

Selectivity of [Cu(thp)$_4$][PF$_6$] (Also Indicated as CP) Towards Cancer Cells Very often, metal complexes have limited clinical use as a result of their systemic toxicity caused by very low selectivity towards cancer cells. The ability to discriminate between normal and malignant cells is of paramount importance for developing clinically applicable chemotherapies.

Evaluating the cytotoxic activity of CP on human non-tumor cell lines, selectivity index (SI=the quotient of the average $IC_{50}$ towards normal cells divided by the average $IC_{50}$ for the relative malignant cells) values about 2- and 3-fold higher than those obtained with CDDP and OXP have been recorded.

TABLE 3

Cytotoxicity towards human non-tumor cells

| | IC$_{50}$ (μM) ± SD | | |
|---|---|---|---|
| | CP | CDDP | OXP |
| MRC-5 | 33.03 ± 1.76 | 19.23 ± 1.35 | 23.13 ± 1.25 |
| HFFF2 | 31.14 ± 3.48 | 20.85 ± 2.33 | 25.54 ± 1.65 |

CP was tested against human lung (MRC-5) and foreskin (HFFF2) fibroblasts. 3-5 × 10$^4$ mL$^{-1}$ cells (depending on the growth characteristics of the cell line) were treated for 72 hrs with increasing concentrations of tested compounds.
The growth inhibitory effect was evaluated by means of MTT test.
IC$_{50}$ values were calculated from the dose-survival curves by four parameter logistic model (P < 0.05).
SD = standard deviation.

TABLE 4

Selectivity index (SI) in human cancer versus human normal cells

| | SI |
|---|---|
| CDDP | 1.7 |
| OXP | 9.3 |
| CP | 32.4 |

SI = quotient of the average IC$_{50}$ values towards normal cells divided by the average IC$_{50}$ values for the malignant cells.

EXAMPLE IV

In Vivo Toxicity Studies of [Cu(thp)$_4$][PF$_6$] (Also Indicated as CP)

To preliminarily establish the toxicity profile of CP, acute and repeat-dose toxicity studies were performed in BALB/c mice and in C57BL mice.

Table 5 indicates that the median lethal doses (LD$_{50}$) calculated for CP were about one order of magnitude higher than that recorded with CDDP.

Table 6, showing the Maximum Tolerated Dose (MTD) values for C57BL mice treated with a single ip administration of different amounts (3.125-6.25-12.5-25-50 mg/kg) of CP or CDDP, clearly suggests that the administration of CP was markedly better tolerated by mice than the reference metallodrug.

TABLE 5

Acute toxicity tests in healthy mice

| | LD$_{50}$ (mg/kg) | |
|---|---|---|
| | BALB/c | C57BL |
| CP | 150$^a$ | 125$^a$ |
| | 135$^b$ | 115$^b$ |
| CDDP | 11$^a$ | 9$^a$ |
| | 9$^b$ | 7$^b$ |

$^a$i.p.;
$^b$e.v.

The acute toxicity was assessed by treating BALB/c or C57BL mice (male; 20-23 g body weight; 6-8 week old) with a single i.p. or e.v. administration of different amounts (3.125-6.25-12.5-25-50-100-200 mg/kg of tested compounds). The animals were observed for 24 hrs for signs of toxicity and mortality.

TABLE 6

Maximum Tolerated Dose

| | MTD (mg/kg) |
|---|---|
| CP | 25.6 |
| CDDP | 4.8 |

The maximum tolerated dose was assessed by treating C57BL mice (male; 20-23 g body weight; 6-8 week old;) with a single ip administration of 1.75, 3.125, 6.25, 12.5, 25, 50 mg/kg of tested compounds). As a sign of toxicity the body weights was measured. MTD based on <20% weight loss and no animal death.

EXAMPLE V

In Vivo Antitumor Activity of [Cu(thp)$_4$][PF$_6$] (Also Indicated as CP)

The antitumor efficacy of CP was evaluated in L1210 murine leukemia and in mouse Lewis Lung carcinoma (LLC). The results demonstrated that CP was safe at a therapeutically effective dose, it showed a favorable pharmacokinetic profile and it was therapeutically effective against the murine solid tumor model.

No significant decreases in body weight as well as no clinical signs of toxicity, including rough coats, hunched posture and dehydration were observed for animals treated with CP.

The antitumor activity of CP in LLC tumor model has been investigated by means of different procedures (early-stage treatment, advanced-stage treatment (1) and advanced-stage treatment (2)) and compared with that promoted by the reference metallodrug, CDDP.

Table 7 shows tumour growth inhibitions induced by CP or CDDP in LLC bearing mice receiving an early-stage treatment. LLC was implanted intramuscularly (i.m., 2×10$^6$ cells inoculum) into the right hind leg of 8-week old inbred C57BL mice (24±3 g body weight) and, after 24 h from tumor implantation, mice were randomly divided into five groups (8 animals per group, 10 controls). CP was dosed at 25, 35 and 50 mk/kg i.p. on days 3, 5, 7, 9, 11 and 13 after tumor implantation. CDDP was dosed at 1.5 mg/kg i.p. on days 3, 5, 7, 9, 11 and 13 after tumor implantation. At day 15, animals were sacrificed, and the inhibition of tumor growth was evaluated.

TABLE 7

Early-stage treatment of an example of solid tumor

| | Daily dose (mg · kg$^{-1}$) | Average tumor weight (mean ± S.D., g) | Inhibition of tumor growth (%) |
|---|---|---|---|
| control$^a$ | — | 0.638 ± 0.01 | — |
| CP | 25 | 0.473 ± 0.12 | 25.86 |
| CP | 35 | 0.273 ± 0.04 | 57.21 |
| CP | 50 | 0.113 ± 0.04 | 82.28 |
| CDDP | 1.5 | 0.168 ± 0.10 | 73.66 |

$^a$vehicle (0.9% NaCl)

Lewis lung carcinoma (LLC) was implanted i.m. (2 · 10$^6$ cells inoculum) into the right hind leg of 8-week old inbred C57BL mice (24 ± 3 g body weight). After 24 h from tumor implantation, mice were randomly divided into five groups (8 animals per group, 10 controls). CP was dosed at 25, 35 and 50 mg/kg ip on days 3, 5, 7, 9, 11 and 13 after tumor implantation. CDDP was dosed at 1.5 mg/kg ip on days 3, 5, 7, 9, 11 and 13 after tumor implantation. At day 15, animals were sacrificed (i.e., before tumor can cause the animal discomfort), the legs were amputated at the proximal end of the femur, and the inhibition of tumor growth was determined according to the difference in weight of the tumor-bearing leg and the healthy leg of the animals expressed as % referred to the control animals.

Mice treated with 50 mg/kg of CP showed a tumor growth inhibition slightly higher to that observed in mice treated with 1.5 mg/kg of CDDP (T/C (%) values growth inhibition of 82.28 and 73.66, respectively). The mice treated with CP (even at the highest doses) showed no significant body weight loss when compared with the non-treated group on the same day. In contrast, the mice treated with CDDP showed about 30% of body weight loss (after the sixth administration)

resulting from the well known CDDP toxicity, as shown in FIG. 1.

The in vivo antitumor activity of CP in LLC tumor model has been further investigated by means of other protocols, such as advanced-stage treatment (1), and advanced-stage treatment (2). For upstaged or advanced stage disease, LLC tumors were allowed to establish and grow to visible (advanced-stage treatment 1) and palpable (advanced-stage treatment 2) size before the start of chemotherapy. The results shown in Table 8 and 9, attested that CP was efficacious even at the lowest dose schedules.

TABLE 8

Advanced-stage treatment (1) of an example of solid tumor

|  | Daily dose (mg · kg$^{-1}$) | Average tumor weight (mean ± S.D., g) | Inhibition of tumor growth (%) |
|---|---|---|---|
| control$^a$ | — | 0.502 ± 0.16 | — |
| CP | 30 | 0.088 ± 0.03 | 82.37 |
| CP | 50 | 0.071 ± 0.02 | 85.85 |
| CDDP | 1.5 | 0.061 ± 0.03 | 87.84 |

$^a$vehicle (0.9% NaCl)
Lewis lung carcinoma (LLC) was implanted int. (2 × 10$^6$ cells inoculum) into the right hind leg of 8-week old imbred C57BL mice (24 ± 3 g body weight). After 24 h from tumor implantation, mice were randomly divided into five groups (8 animals per group, 10 controls). Chemotherapy was delayed until the tumor became visible (day 7). From day 7, CP was dosed daily at 30 and 50 mg/kg i.p. whereas CDDP was dosed daily at 1.5 mg/kg i.p.. At day 15, animals were sacrificed (i.e., before tumor can cause the animal discomfort), the legs were amputated at the proximal end of the femur, and the inhibition of tumor growth was determined according to the difference in weight of the tumor-bearing leg and the healthy leg of the animals expressed as % referred to the control animals.

TABLE 9

Advanced-stage treatment (2) of an example of solid tumor

| Compound | Daily dose (mg · kg$^{-1}$) | Average tumor weight (mean ± S.D., g) | Inhibition of tumor growth (%) |
|---|---|---|---|
| control$^a$ | — | 0.432 ± 0.21 | — |
| CP | 50 (days 9-11) 30 (days 12-14) | 0.024 ± 0.03 | 94.44 |
| CDDP | 1.5 | 0.118 ± 0.10 | 72.68 |

$^a$vehicle (0.9% NaCl)
Lewis lung carcinoma (LLC) was implanted i.m. (2 × 10$^6$ cells inoculum) into the right hind leg of 8-week old imbred C57BL mice (24 ± 3 g body weight). After 24 h from tumor implantation, mice were randomly divided into five groups (8 animals per group, 10 controls). Chemotherapy was delayed until the tumor became palpable (day 9). From day 9 to day 11, CP was dosed daily at 50 mk/kg ip whereas from day 12 to day 14 at 30 mg/kg ip. CDDP was dosed daily at 1.5 mg/kg ip. At day 15, animals were sacrificed (i.e., before tumor can cause the animal discomfort), the legs were amputated at the proximal end of the femur, and the inhibition of tumor growth was determined according to the difference in weight of the tumor-bearing leg and the healthy leg of the animals expressed as % referred to the control animals.

EXAMPLE VI

Biodistribution Studies in Solid Tumor Bearing Mice

Figure 4:
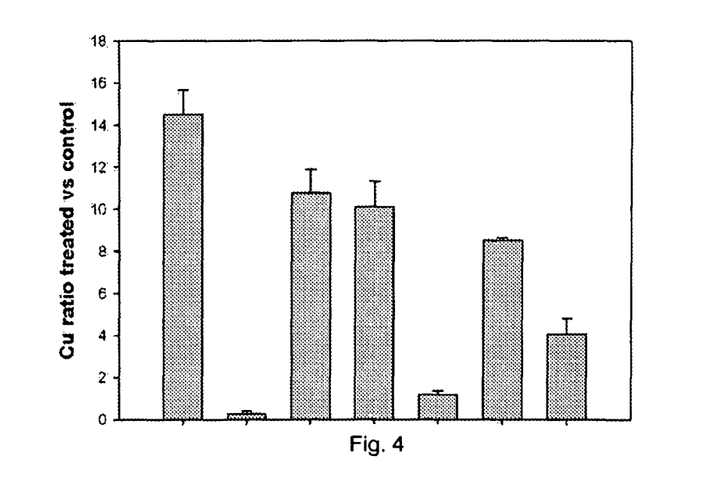
FIG. 4 shows a chart of tissue distribution in LLC bearing C57BL mice. Mice were inoculated i.p. on the right flank with 2×10$^6$ LLC cells. After 10 days, CP was administered i.p. at a dose of 50 mg/kg. The mice were sacrificed after 24 hours and tumor (indicated with 1), brain (indicated with 2), spleen (indicated with 3), kidney (indicated with 4), intestine (indicated with 5), liver (indicated with 6) and stomach (indicated with 7) were excised. Tissues were washed in ice-cold saline and weighed after removing excess fluid. All samples were mineralized in $HNO_3$ and Cu content in each sample was measured by atomic absorption spectrophotometry. The Y axis indicates the ratio of copper amount in treated versus control mice.

To assess the potential selectivity to the solid tumor mass, tissue distribution of [Cu(thp)$_4$][PF$_6$] (CP) was investigated in LLC bearing C57BL mice. On day 10 after tumor implantation, mice were treated with a single i.p. injection of 50 mg/kg of CP. The tissue distribution of CP at 24 hrs post i.p. injection can is shown in FIG. 4.

The invention claimed is:

1. A method for the treatment of at least a solid tumor and/or refractory solid tumor selected from the group consisting of pancreas, bone, brain and stomach tumors in humans by means of the administration at an effective dose of a Cu(I) complex of the type [Cu(thp)$_4$]$_n$[X]$_{-n}$ wherein thp is a tris(hydroxymethyl)phosphine and X comprises N$_3$ (azide), PF$_6$, NO$_3$, NO$_2$, ClO$_4$, Cl, Br, I, C$_6$H$_{11}$(CH$_2$)$_3$CO$_2$ (cyclohexanebutyrate), D-gluconate, CH$_3$COO, CF$_3$COO, HCOO, C$_5$HF$_6$O$_2$ (hexafluoroacetylacetonate), C$_5$H$_4$F$_3$O$_2$ (trifluoroacetylacetonate), BF$_4$, CF$_3$SO$_3$, BH$_4$, HBpz$_3$ (pyrazolylborates), HBtz$_3$ (triazolylborates), CH$_3$(CH$_2$)$_{11}$OSO$_3$ (dodecylsulfate), C$_4$H$_9$(C$_2$H$_5$)CHCOO (2-ethylhexanoate), B(C$_2$H$_5$)$_4$ (tetraethylborate), C$_{17}$H$_{35}$COO (stearate), B(C$_6$H$_5$)$_4$ (tetraphenylborate), BH(CH$_3$COO)$_3$ (triacetoxyborohydride), CB$_{11}$H$_6$Br$_6$ (hexabromocarborane), C$_{10}$H$_{19}$O$_3$ (neodecanoate), SCN (thiocyanate), C$_{11}$H$_{19}$O$_2$ (TMHD) for n=1, X comprises PO$_3$F (fluorophosphate), SiF$_6$ (hexafluorosilicate), C$_2$O$_4$ (oxalate), SeO$_3$ (selenite), S (sulfide), SO$_3$ (sulfite), B$_4$O$_7$, SiO$_3$ (metasilicate), HPO$_4$, CO$_3$, SO$_4$ for n=2, X comprises PO$_4$ for n=3 and X comprises SiO$_4$ (orthosilicate) for n=4.

2. The method according to claim 1, wherein said Cu(I) complex of the type [Cu(thp)$_4$]$_n$[X]$_{-n}$ is [Cu(thp)$_4$][PF$_6$].

3. The method according to claim 2, wherein said administration occurs in aqueous solution or orally or subcutaneously or parenterally.

4. The method according to claim 1, wherein said administration occurs in aqueous solution or orally or subcutaneously or parenterally.

* * * * *